US005591823A

United States Patent [19]
Hung et al.

[11] Patent Number: 5,591,823
[45] Date of Patent: Jan. 7, 1997

[54] EXPRESSION OF SPECIFIC IMMUNOGENS USING VIRAL ANTIGENS

[75] Inventors: Paul P. Hung, Bryn Mawr; Shaw-Guang L. Lee, Villanova; Narender K. Kalyan, Wayne, all of Pa.

[73] Assignee: American Home Products Corporation, Madison, N.J.

[21] Appl. No.: 169,813

[22] Filed: Dec. 17, 1993

Related U.S. Application Data

[63] Continuation-in-part of Ser. No. 805,105, Dec. 11, 1991, abandoned.

[51] Int. Cl.$^6$ ............................. C07K 1/00; C12Q 1/70; A61K 39/00; A61K 39/145
[52] U.S. Cl. .................. 530/350; 424/184.1; 424/188.1; 424/206.1; 424/208.1; 424/209.1; 424/201.1; 435/5
[58] Field of Search ........................ 424/184.1; 530/350

[56] References Cited

U.S. PATENT DOCUMENTS 5,166,057  11/1992  Palese et al. ........................... 435/69.1

FOREIGN PATENT DOCUMENTS 0339504  11/1989  European Pat. Off. .......... C07K 7/00
9103552   3/1991  WIPO ............................. C12N 15/11

OTHER PUBLICATIONS

Koff, et al, 1988, "Development and Testing of AIDS Vaccines" Science 241:426–432.
Cohen, et al, 1993, "Jitters Jeopardize AIDS . . . " Science 262:980–981.
Baldari, et al. "Plasmids pEMBLY: New Single-Stranded Shuttle Vectors for the Recovery and Analysis of Yeast DNA," Gene, 35:27–32, 1985.
Berzofsky, J. A., et al., "Approaches and Issues in the Development of Vaccines Against HIV," Journal of Acquired Immune Deficiency Syndromes, 4:451–459, 1991.
Bolognesi, "Progress in Vaccine Development Against SIV and HIV," Journal of Acquired Immune Deficiency Syndromes, 3:390–394, Raven Press, Ltd., NY, 1990.
Chou, et al., "Prediction of Protein Conformation", Biochemistry, 13:222–245, 1974.
Colbere-Garapin, et al., "Addition of a Foreign Oligopeptide to the Major Capsid Protein of Poliovirus", Proc. Natl. Acad. Sci., USA, 85:8668–8672, Nov. 1989.
Crea, et al., "Chemical Synthesis of Genes for Human Insulin," Proc. Natl. Acad. Sci., USA, 70:5765, 1978.
Current Protocol in Molecular Biology, John Wiley & Son, 1989.
Evans, et al., "An Engineered Poliovirus Chimaera Elicits Broadly Reactive HIV–1 Neutralizing Antibodies", Nature, 339:385–388, Jun. 1989.
Germann, et al., "Expression of a Multidrug Resistance–Adenosine Deaminase Fusion Gene", Journal of Biological Chemistry, 264:7814–7824, 1989.

Gheysen, et al., "Assembly and Release of ZHIV–1 Precursor Pr55gag Virus–like Particles from Recombinant Baculovirus–Infected Insect Cells", Cell, 59:103–112, 1989.
Hartman, et al., "Human Influenza Virus Hemagglutinin is Expressed in Monkey Cells Using Simian Virus 40 Vectors," Proc. Natl. Acad. Sci, USA, 79:233–237, 1982.
Hiti, et al., "Complete Sequence Analysis Shows That the Hemagglutinins of the HO and H2 Subtypes of Human Influenza Virus are Closely Related", Virology, 111:113–124, 1981.
Ho, et al., "Second Conserved Domain of gp120 Is Important for HIV Infectivity and Antibody Neutralization", Science, 239:1021–1023, Feb. 26, 1988.
Hopp, et al., "Prediction of Protein Antigenic Determinants from Amino Acid Sequences", Proc. Natl. Acad. Sci, USA, 78:3824–3828, 1981.
Javaherian, et al., "Principal Neutralizing Domain of the Human Immunodeficiency Virus Type 1 Envelope Protein," Proc. Natl. Acad., Sci. USA, 86:6768–6772, 1989.
Michel, et al., "Induction of Anti–Human Immunodeficiency Virus (HIV)–Neutralizing Antibodies in Rabbits Immunized with Recombinant HIV–Hepatitis B Surface Antigen Particles", Proc. Natl. Acad. Sci, USA, 85:7957–7961, 1988.
Modrow, et al., "Computer–Assisted Analysis of Envelope Protein Sequences of Seven Human Immunodeficiency Virus Isolates: Prediction of Antigenic Epitopes in Conserved and Variable Regions", Journal of Virology, 61:570–578, 1987.
Posse, "Cell–Surface Expression of Influenza Virus Haemagglutinin in Insect Cells Using a Baculovirus Vector", Virus Research, 5:43–59, 1986.
Rusche, et al., "Antibodies that Inhibit Fusion of Human Immunodeficiency Virus–Infected Cells Bind a 24 Amino Acid Sequence of the Viral Epitope", gp120, Proc. Natl. Acad. Sci, USA, 85:3198–3202, May 1988.
Sambrook, et al., Molecular Cloning, A Laboratory Manual, Cold Spring Harbor Laboratory Press, 1989.
Smith, et al., "Production of Heman Beta Interferon in Insect Cells Infected with Baculovirus Expression Vector," Molecular and Cellular Biology, 3:2156–2165, Dec., 1983.
Stanworth, et al., "Allergy Treatment with a Peptide Vaccine", The Lancet, 336:1279–1281, Oct. 7, 1990.

(List continued on next page.)

Primary Examiner—Lynette F. Smith
Attorney, Agent, or Firm—Richard K. Jackson

[57] ABSTRACT

Chimeric DNA fragments are provided which include a nucleotide sequence substantially the same as that which codes for the HA surface protein of an influenza A virus having five immunodominant antigenic sites, wherein a nucleotide sequence substantially the same as that which codes for a foreign epitope is inserted into the nucleotide sequence of an antigenic site. Corresponding chimeric peptides, expression vectors, and transformed hosts are provided as well. These peptides are useful in providing vaccines against the respective antigens and in test kits to detect the exposure to such antigens. Additionally, these peptides or their corresponding antibodies are useful in methods of treatment and prevention of the manifestations of exposure to these antigens, including immunotherapy.

9 Claims, 2 Drawing Sheets

OTHER PUBLICATIONS

Stanworth, et al., "The Role of High and Low Affinity IgE Receptors in Cell Signalling Processes", Molecular Immunology, 27(12):1291–1296, 1990.

Stanworth, "The Role of Non–Antigen Recptors in Mast Cell Signalling Processes", Molecular Immunology, 21:1183–1190, 1984.

Summers, et al., A Manual of Methods for Baculovirus Vectors and Insect Cell Culture Procedures, Texas A&M University, College Station, TX, 1988.

Vialard, et al., "Synthesis of Membrane Fusion and Hemagglutinin Proteins of Measles Virus, Using Novel Baculovirus Vector Containing the β–Galactosidase Gene", Journal of Virology, 69:37–50, Jan. 1990.

Wain–Hobson, "Nucleotide Sequence of the AIDS Virus, LAV", Cell, 40:9–17, Jan., 1985.

Wiley, et al., "The Structure and Function of the Hemagglutinin Membrane Glyco–protein of Influenza Virus", Ann. Rev. Biochem., 56:365–394, 1987.

Wiley, et al., "Structural Identification of the Antibody–Binding Sites of Hong Kong Influenza Haemagglutinin and Their Involvement in Antigenic Variation", Nature, 289:373–378, 1981.

Wilson, et al., "Structure of the Haemagglutinin Membrane Glycoprotein of Influenza Virus at 3Å Resolution", et al., Nature, 289:366–373, 1981.

Wu, et al., "Expression of Immunogenic Epitopes of Hepatitis B Surface Antigen with Hybrid Flagellin Proteins by a Vaccine Strain of Salmonella", Proc. Natl. Acad. Sci, USA, 86:4726–4730, Jun. 1989.

EXPRESSION OF SPECIFIC IMMUNOGENS USING VIRAL ANTIGENS

RELATED APPLICATIONS

This application is a continuation-in-part of U.S. patent application Ser. No. 07/805,105, filed Dec. 11, 1991, by Paul P. Hung, Shaw-Guang L. Lee and Narender K. Kalyan, now abandoned.

FIELD OF THE INVENTION

This invention relates to influenza virus hemagglutinin (HA) chimeric proteins which can be used as vaccines against viruses, pathogenic bacteria, or other antigens such as those specific for cancerous tissues, allergic responses, and the like. These chimeric proteins can also be used in treatment of the manifestations of such antigens and in the detection of such antigens or related antibodies. Nucleotide sequences coding for such proteins are provided as well.

Foreign epitopes such as human immunodeficiency virus epitopes are inserted into the antigenic sites of the HA protein, and these chimeric proteins are capable of inducing specific immune responses against the inserted epitope.

BACKGROUND OF THE INVENTION

Many approaches are used in the preparation of vaccines. For viral diseases, these methods include the use of inactivated viruses, live viruses, live recombinant viruses, viral proteins, viral subunit proteins and the like.

However, many types of vaccines have limited success in part because of the extensive genetic variation from one strain or isolate of an organism to another. Additionally, human or animal antigens involved in pathogenesis, i.e. IgE for allergic reactions, tumor antigens, etc., do not produce beneficial immune responses in the same animal species from which they are derived, and indeed may be treated as self-proteins, and not as antigens.

However, it is desirable to use small peptide sequences or epitopes (i.e., antigenic determinants) representing the biological function of a given antigen as immunogens even in homologous animal species. In theory, these peptides can be used to elicit an immune response when injected into animals. In practice, however, these peptides are often not good immunogens because they are usually small and do not present themselves favorably to the immune system.

An example of such a poorly immunogenic peptide is the second conserved domain of the external envelope glycoprotein (gp120) of the human immunodeficiency virus (HIV). It has been found to be important for HIV infectivity and antibody neutralization. *Science,* 239:1021–1023, Feb. 26, 1988. Antiserum directed against this region (amino acids 254–274) can neutralize three different isolates of HIV in vitro, without affecting the binding of the virus to T-cell receptor or CD4-positive cells. The conserved domain is believed to be critical in a post binding event during virus penetration and could be a potential target for antibody neutralization. However, it has been observed that this domain is relatively "immunosilent" when it is presented to the immune system in the context of natural HIV infection. This kind of immunosilence suggests that the epitope may be masked, for example, by protein configuration.

Further details of HIV antigens can be found in Rusche, et at., "Antibodies that Inhibit Fusion of Human Immunodeficiency Virus-infected Cells Bind a 24 Amino Acid Sequence of the Viral Envelope, gp120," *Proc. Natl. Acad. Sci. USA,* 85:3198–3202, May 1988; Bolognesi, "Progress in Vaccine Development Against SIV and HIV," *Journal of Acquired Immune Deficiency Syndromes,* 3:390–394, Raven Press, Ltd., New York, 1990; Wain-Hobson, "Nucleotide Sequence of the AIDS Virus, LAV," *Cell,* 40:9–17, January 1985; and Ho, et al, "Second Conserved Domain of gp120 Is Important for HIV Infectivity and Antibody Neutralization," *Science,* 239:1021–1023, Feb. 26, 1988.

One way to enhance the immunogenicity of epitope peptides is to increase their size, and therefore their recognizability, by linking them in some manner to fusion proteins, macromolecules, or adjuvants.

Colbere-Garapin et at. have reported the preparation of insertion mutants of type poliovirus (Sabin strain), in which additional amino acid sequences (tri- or hexapeptides) are inserted within the neutralization site 1 of the capsid protein VP1. Colbere-Garapin, et al., "Addition of a Foreign Oligopeptide to the Major Capsid Protein of Poliovirus," *Proc. Natl. Acad. Sci. USA,* 85:8668–8672, November 1989.

Evans, et al., have reported the construction and the characterization of a poliovirus antigenic chimera protein containing an epitope from the transmembrane glycoprotein (gp41) of human immunodeficiency virus type 1 (HIV-1). Rabbit antisera raised by subcutaneous injection of live polio/HIV chimera was shown to be broadly neutralizing against several American and African HIV-1 isolates. Evans et al., "An Engineered Poliovirus Chimaera Elicits Broadly Reactive HIV-1 Neutralizing Antibodies," *Nature,* 339:385–388, Jun. 1, 1989. However, the use of live viral vectors such as polio virus presents problems for practical use, in that serum antibodies may arrest replication of recombinant virus in the body. In addition, live viral vectors have rigid constraints on the size of an insert and provide a limited number of insertion sites.

Wu, et al., have reported the in-frame insertion of synthetic oligonucleotides corresponding to amino acid residues of S (122–137) and pre-$S_2$ (120–145), which are hepatitis B virus surface antigens, into the hypervariable region of a cloned Salmonella flagellin gene. Animals immunized with the live recombinant bacteria developed antibodies specific to the hepatitis B virus epitopes as detected by ELISA. Wu, et al., "Expression of Immunogenic Epitopes of Hepatitis B Surface Antigen with Hybrid Flagellin Proteins by a Vaccine Strain of Salmonella," *Proc. Natl. Acad. Sci. USA,* 86:4726–4730, June 1989. The immune response was weak, short-lived, and declined rapidly after immunization.

Cohen reported in Science, 262 980 (Nov. 12, 1993), the comments of speakers at the annual AIDS vaccine conference to the effect that although effective immunization toward HIV that was grown in laboratory cell lines may be achieved, immunization toward freshly harvested HIV was not so effected. From this report, even though Barbara Potts from New York's United Biomedical Inc. reported some success, one may conclude that development of strain specific vaccines or vaccine cocktails designed to immunize against a range of HIV antigens may be necessary for effective immunization.

Michel, et al., have reported the insertion of various HIV envelope fragments into the hepatitis B virus surface antigen. Immunization of rabbits with these fusion proteins produced neutralizing antibodies. Michel, et al., "Induction of Anti-Human Immunodeficiency Virus (HIV) Neutralizing Antibodies in Rabbits Immunized with Recombinant HIV-Hepatitis B Surface Antigen Particles," *Proc. Natl. Acad. Sci. USA,* 5:7957–7961, 1988.

Similarly, it has been found that histamine release from rat mast cells, both in vitro and in vivo, can be inhibited by immunization with a human peptide-protein conjugate. Stanworth, et al., "Allergy Treatment with a Peptide Vaccine," *The Lancet*, 36:1279–1281, Oct. 7, 1990. See also, Stanworth, et al., "The Role of High and Low Affinity IgE Receptors in Cell Signalling Processes," *Molecular Immunology*, 27(12):1291–1296, 1990.

Monoclonal antibodies (mAbs) have also been widely used for passive immunization and for diagnostic purposes to detect infections or pathologic conditions like the presence of tumor antigens. However, production of a monoclonal antibody of desired specificity is laborious and unpredictable. Several steps of blind screening and assays involving a series of overlapping peptides are needed to determine specificity of an mAb. Sometimes the functional epitope may not be in the immunodominant position for the antigen to produce an mAb against that region.

Thus, there is a need for vaccines, diagnostic agents, and therapeutic agents that can take advantage of the potential immunogenicity of antigenic determinants or epitopes according to the invention.

SUMMARY OF THE INVENTION

Chimeric proteins have now been discovered which are immunogenic and comprise the HA protein of influenza A virus having a foreign epitope insertion. Immunization of mammals with these recombinant or synthetic chimeric proteins results in the generation of peptide specific antibodies. The immune response generation with these chimeric proteins is long-lasting, for example, in excess of six months. These chimeric proteins, alone or in combination with sequentially or structurally (stereo-conformers) related proteins, or the corresponding antibodies can also be utilized as diagnostic tools and as immunotherapy against infections in pathologic conditions as well as in post-exposure cases, like accidental pricking with needles in hospitals.

DNA fragments which code for HA chimetic proteins have also been discovered. These fragments comprise a nucleotide sequence substantially the same as that which codes for the HA surface protein of the influenza A virus having five immunodominant antigenic sites. According to the invention, a nucleotide sequence substantially the same as that which codes for a foreign epitope is inserted into the nucleotide sequence which codes for at least one of the antigenic sites.

Also contemplated are peptides comprising an amino acid sequence substantially the same as the HA surface protein of the influenza A virus having five immunodominant antigenic sites, wherein an amino acid sequence substantially the same as a foreign epitope is inserted into the amino acid sequence for at least one of the immunodominant antigenic sites.

These proteins can be administered in effective amounts, alone or in conjunction with other antigenic proteins, to mammals (including humans) in need, for the treatment or the prevention of various pathologies. Additionally, those peptides or corresponding antibodies can be used to detect exposure of a mammal, preferably through blood or a fraction thereof, to various antigens. Vaccines containing the above peptides; expression vectors comprising the above DNA fragments, particularly baculovirus; and transformed microorganism hosts are all encompassed by the present invention.

DETAILED DESCRIPTION OF THE INVENTION

This invention concerns the synthesis, expression, and use of novel DNA and peptides, and the DNA and peptides themselves, comprising an epitope-inserted HA influenza surface protein.

A. HA Influenza Protein

The HA surface protein of influenza A virus is one of two surface proteins of the influenza A virus. Neuraminidase (NA) is the other. HA is the major surface glycoprotein of the virus and is the antigen against which neutralizing antibodies are directed. HA is also responsible for the attachment of the virus to cell receptors, and therefore, is responsible for initiation of viral infection. Influenza A virus causes frequent epidemics due to extensive antigenic variation of the virus. These variations are due to amino acid changes in major antigenic sites of HA.

Various HA genes of different influenza strains have been cloned, and all are suitable for use in the present invention. Particular note is made of the HA gene of the A/WSN/33 strain. This gene is 1775 nucleotides in length and codes for 565 amino acids. Hiti, et al., *Virology*, 111:113–124, 1981.

Analysis of the amino acid sequence deduced from the nucleotide sequence shows the presence of a signal peptide (17 amino acid residues) which is cleaved off during the secretion process of HA. Mature HA has two subunits, HA1 (325 residues) and HA2 (222 residues), connected by a single arginine residue, which is cleaved off during maturation to give rise to two-chain HA. The amino acid sequence (512–530) at the C-terminus is very hydrophobic and probably constitutes the transmembrane region of HA. There are seven potential glycosylation sites. HA exists as a trimer and is mainly comprised of two distinct structural regions, a fibrous coil system of alpha helixes extending 76 angstroms from the membrane, and a globular region of antiparallel beta-sheet which contains the receptor binding site and the variable antigenic sites positioned on top of this stem.

A comparison with other flu viral subtypes indicates that many stretches of the sequence, including all of the cysteines, are conserved in all strains. This suggests that a basic structure of HA is required for its functional activity. The amino acid sequence in HA2 is more conserved than that in HA1, and interstrain variations are due to changes in HA1 sequences. Hiti, et al., *Virology*, 111:113–124, 1981; Wiley, et al., *Nature*, 289:373–378, 1981.

Figure 1:
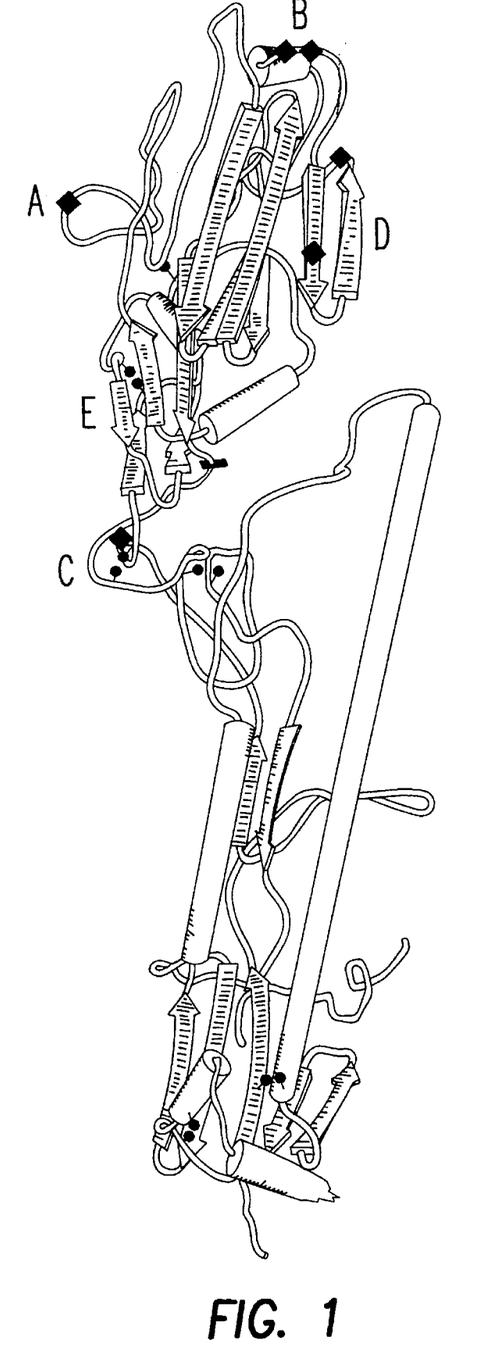
FIG. 1 is a diagram of the HA protein of influenza A virus.

The three dimensional structure of HA protein is illustrated in Wilson, et al., *Nature*, 289:366–373, 1981 (see FIG. 1). It has five antigenic sites, A, B, C, D, and E, surrounding the receptor binding site, which is present as a concave pocket. In HA of influenza virus strain A/WSN/33, the locations of the corresponding five antigenic sites are identified as follows: Site A (aa 136–142) is a protruding loop region. Site B (aa 183–192) is a region of external residues in an alpha helix. Site C is a bulge in the tertiary structure at the disulfide bond between cys 42 and cys 274. Site D is a buried region in the interface between subunits spanning from aa 197–216, and Site E is from aa 52–74. At least one amino acid substitution in each of five antigenic sites appears to be required to generate new epidemic flu strains.

Additionally, antibodies directed to these five antigenic sites have been observed to neutralize viral infectivity. It is believed that site A, due to its accessibility, is well suited for high activity neutralizing antibody. Wiley, et al., *Nature*, 289:373–378, 1981; Wiley, et al., *Ann. Rev. Biochem.*, 56:365–394,1987.

In the present invention, HA protein is used as a vehicle to carry non-HA or foreign epitopes. Insertion into HA preferably occurs at one or more of these five antigenic regions and most preferably occurs at the A region. A further preferred insertion site is the region defined by amino acids 183–192.

B. Exemplary Foreign Epitopes

Foreign epitopes useful in the present invention include any epitope known to those of ordinary skill in the art other than HA protein epitopes. Peptide and nucleotide sequences that are substantially the same as those corresponding to a naturally occurring epitope are useful in the present invention as well.

Examples of foreign epitopes include, but are not limited to, viral epitopes (such as HIV-1 epitopes, hepatitis B epitopes, hepatitis C epitopes, retrovirus epitopes, and *Herpes simplex* virus epitopes); bacterial protein epitopes; IgE effector site epitopes (which are instrumental in allergies); SP10 epitope (a pregnancy antigen); tumor epitopes including breast cancer epitopes; and any other antigenic epitopes of pathological importance as well as neutralizing proteins thereof or immunogenic portions thereof.

The term "immunogenic portion" is meant to include portions of a protein that are immunogenic in any condition, including those that are immunosilent before insertion but which become immunogenic or antigenic upon fusion with an HA protein. Methods of identifying such peptides or epitopes are known. Chou, et al., *Biochemistry*, 13:222–245, 1974; Hopp, et al., *Proc. Natl. Acad. Sci. USA*, 78:3824–3828, 1981.

The term "substantially the same as" includes identical nucleotide or amino acid sequences as well as sequences modified by biological, genetic, or clinical techniques which possess substantially the same biological activity. In the case of a nucleotide sequence, the biological activity could be, for example, the ability to code for an epitope which will elicit corresponding antibody promotion. In the case of an amino acid sequence, the ability to elicit corresponding antibody formation would be one example. Such activity is assayed by methods known to those of ordinary skill in the art including but not limited to immunofluorescence, ELISA, Western blot, autoradiography, and the like.

1. HIV Epitopes

One class of foreign epitope for insertion into HA according to the invention is that of the HIV-1 virus. HIV is the causative agent for Acquired Immune Deficiency Syndrome (AIDS). The HIV-1 genome codes for three viral structural proteins in three regions, the gag region, the pol region and the env or viral envelope region. The gag region produces viral core proteins.

The major core proteins are initially synthesized as precursor protein p55. P55 is subsequently processed into p17, p24, p15 (p9 and p6) by a viral protease encoded by the pol region. The gag precursor is thought to play a critical role in the assembly of viral particles at the plasma membrane. Gheysen, et al., *Cell*, 59:103–112, 1989. Like most retroviral gag proteins, p55 (and p17 after processing) is myristylated at its N-terminal.

P24 is present on the inner core of HIV. P17 appears to be located on the inner side of the lipid membrane, and P15, because of its highly basic character, is probably associated with the HIV genome. P24 is one of the earliest HIV proteins detected in AIDS patients, and antibodies against p24 and p17 are present in all AIDS patients. It is thought that core proteins, i.e. gag, can produce cell mediated immunity.

The pol region of HIV-1 codes for reverse transcriptease, protease, and endonuclease proteins.

The env region transcribes envelope protein gp160, which is processed into gp120 and gp41. The major envelope protein, gp120, is located on the outer surface of the virion as "spikes," and the transmembrane protein gp41 includes a membrane anchor sequence and serves as the attachment site for gp120 on the surface of HIV-1. Gp120 contains the T-cell receptor (CD4) binding site as well as major sites recognized by neutralizing antibodies.

Recombinant gp120 or gp160 elicit low titered neutralizing antibodies after repeated injections. The principal neutralizing determinant of HIV is located on the hypervariable region of the gp120 V3 loop (amino acids 303–338). The antibodies produced by this peptide are viral variant specific. Javaherian, et al., *Proc. Natl. Acad. Sci. USA*, 86:6768–6772, 1989.

A range of antigenically distinct HIVs have been isolated from the same infected individual. Nucleotide sequence analysis has also demonstrated that there is considerable variation in HIV-1 isolates. These variations appear to be concentrated in gp120 and allow the virus to evade most immune surveillance mechanisms. The majority of predicted antigenic epitopes in gp120 are found in regions of high sequence variability and are interspersed in highly conserved regions. Modrow, et al., *J. Virology* 61:570–578, 1987. The gag and pol sequences do not have highly variable regions.

Several approaches have been taken to produce AIDS vaccines, e.g. inactivated virus, live recombinant virus, viral subunit proteins, etc. These have so far met with limited success, partly because of genetic variation from one HIV isolate to another. Indeed, it is believed that about 25% of the amino acids in the envelope can mutate. The conserved regions of HIV have proven to be "immunosilent" when presented to the immune system in the context of gp120, in contrast to their immunogenicity as synthetic oligopeptides as explained above. The epitopes comprising the conserved regions of HIV, which are typically immunosilent, can become immunogenic when inserted into one or more of the antigenic sites of HA according to the invention.

Several HIV epitopes suitable for the present invention are listed in Table 1 below:

TABLE 1

| HIV EPITOPES | | |
|---|---|---|
| PEPTIDE[A] | LOCATION | COMMENTS |
| 1. T 20 E | env255–274 | Second conserved region of env; produces neutralizing antibodies. |
| 2. T 16 G | env255–270 | |
| 3. D 18 S | env gp41 735–752 | Very hydrophilic; neutralized several HIV-1 strains; inhibits syncytia formation. |
| 4. G 20 E | protease active site | Highly conserved in all HIV strains |
| 5. K 27 R | env403–429 | CD4 binding domain; |
| 6. E 14 Q | env414–427 | Immunosilent; conserved; antibody produced vs. peptide is neutralizing. |

TABLE 1-continued

HIV EPITOPES

| PEPTIDE[A] | LOCATION | COMMENTS |
| --- | --- | --- |
| 7. N 22 G (K17K) | env307–330 | Major immuno-dominant epitope, but highly variable; . . . HIGPGRAFY sequence produces neutralizing antibody. |
| 8. p17 | gag86–115 | Conserved; produce T-cell response. |
| 9. p24 | gag281–305 | |

[A]Peptides are named to indicate the size of the peptide and the first and the last amino acid of that peptide. All but one epitope are from the conserved region of the viral proteins. The epitopes, N22G and its 5 amino acid smaller analogue K17K, corresponds to the hypervariable region of gp120 called the V3 loop.

2. IgE Epitopes

Another epitope suitable for use in the invention is a part of immunoglobulin IgE, which is present in low concentrations in blood. IgE consists of two chains, heavy and light. IgE is a minor component of total serum immunoglobulins and mediates immediate types of hypersensitivities responsible for allergic reactions including, but not limited to, hay fever, asthma, food and drug allergies, and the like. The role of IgE in triggering allergic response was studied with synthetic rat epsilon or heavy chain peptides and antipeptide antibodies. Stanworth, *Molecular Immunlogy*, 21:1183–1190, 1984; Stanworth, et al., *Molecular Immunology*, 27:1291–1296, 1990. Circulating IgE binds to the high affinity IgE Fc receptor (FcεRI) which is expressed on the surface of mast cells and basophils. In an IgE-mediated response, cross-linking of receptor-bound IgE by a multivalent allergen leads to aggregation of the underlying FcεRI receptors which in turn triggers the release of histamine and other chemical modulators of an allergic response. Repeated exposure to an allergen results in the increased production of specific IgE and thereby increased, and sometimes fatal, allergic responses. Monoclonal and polyclonal antibodies are potent allergens by virtue of their ability to cross-link the IgE bound receptor.

IgE also binds to a low affinity IgE Fc receptor (FcεRII) which is present in B and T cells. This receptor, also known as CD23, is believed to play an important the synthesis of IgE in B cells.

It was found that sites responsible for the binding to the receptor and the one for effector activity reside at different parts of the IgE molecule. While the binding site resides within both the CH3 and CH4 domains of IgE, the effector or trigger site is located in the CH4 domain. The peptide of the trigger site is characterized by an N-terminal cationic "head" separated by three amino acids from the hydrophilic tail. Research has indicated that this peptide mediates the immunological triggering signal in mast cells in response to allergen challenge. Stanworth, et at., *Lancet*, 336:1279–1281, 90. The amino acid sequence of this peptide is: Lys-Thr-Lys-Gly-Ser-Gly-Phe-Phe-Val-Phe and correspond to amino acids 497–506 of the human IgE heavy chain. It can be synthesized from two complementary oligonucleotides:

| | K | T | K | G | S | G | F | F | V | F | | |
| --- | --- | --- | --- | --- | --- | --- | --- | --- | --- | --- | --- | --- |
| 5' | AAA | ACC | AAG | GGA | TCA | GGA | TTC | TTT | GTA | TTC | GGG | GCC 3' |
| CCGG | TTT | TGG | TTC | CCT | AGT | CCT | AAG | AAA | CAT | AAG | CC | |
| | | | Sty 1 | | | | | | | | | Apa 1 |

This epitope is found in the nucleotide sequence coding for H22V having the amino acid sequence HSTTQPRKT-KGSGFFVFSRLEV. This peptide can be the synthesized from the nucleotide sequence:

| Apa 1 | H | S | T | T | Q | P | R | K | T | K | | |
| --- | --- | --- | --- | --- | --- | --- | --- | --- | --- | --- | --- | --- |
| | CAC | AGT | ACT | ACA | CAG | CCC | CGC | AAA | ACC | AAG | | |
| CCGG | GTG | TCA | TGA | TGT | GTC | GGG | GCG | TTT | TGG | TTC | | |
| G | S | G | F | F | V | F | S | R | L | E | V | |
| GGA | TCA | GGA | TTC | TTT | GTA | TTC | TCA | CGC | CTA | GAG | GTG | GCC |
| CCT | AGT | CCT | AAG | AAA | CAT | AAG | AGT | GCG | GAT | CTC | CA | |

C. HA-Chimeric Peptide

The HA-chimeric peptides of the present invention can be used as vaccines to produce peptide specific antibodies which incorporate a mixture of specificities against several sequences within that peptide. These antibodies are of high affinity and are suitable for diagnosis as well as immunotherapy. Peptides within the scope of the present invention can also be administered prophylactically to prevent infection. Administration as a vaccine or for immunotherapy can be by any means known to those of ordinary skill in the art including, but not limited to, oral, rectal, nasal, buccal, or parenteral administration. Vaccines or pharmaceutical compositions for use in immunotherapy may also include any pharmaceutically acceptable carrier or adjuvant commonly used in the art.

One or more epitopes can be inserted in any HA chimera to provide di-, tri-, tetra- or penta- valent chimera HA. The epitope at each insertion site may be the same or different. If the epitope is the same, greatly increased antibody response will be seen over the mono-valent HA chimera. If the epitope is different, a multi-antibody response will result. More than one copy of one epitope and one or more other epitopes could also be inserted to yield increased antibody response and multi-antibody response. One application of this approach is the design of a multiple vaccine that can be used as a vaccination against several diseases or disease strains simultaneously.

The effective amount of peptide in each application can be determined by means known to one of ordinary skill in the art. For example, optimum dosage can be established using serially diluted preparations of the active agents of the present invention in connection with a suitable testing procedure. Alternatively, a matrix of dosages and frequency of administration can be established and groups of experimental subjects can be assigned to each part of the matrix in order to determine the optimum conditions.

Typically in a vaccine, HA-epitope chimeric antigens are mixed thoroughly with an adjuvant, i.e. SYNTEX adjuvant or alum, and about 1–100 μg are injected into a host. The host can be boosted periodically, i.e. every 4 weeks, until a high-titer antibody against the peptide is obtained. More than one similar or dissimilar HA-epitope protein can be combined in a single vaccine. Vaccine preparation typically involves the insertion of HA gene, with foreign epitope sequences such as an HIV epitope sequence, in a suitable expression vector. The new protein is expressed in tissue culture, and the chimeric protein is isolated. Suitable animals are then vaccinated.

The HA-epitope antigens of the present invention are also useful for the diagnosis of antigen exposure or viral infection. ELISA is the most commonly used method to detect the presence of infecting viral antigens in the blood as described in *Current Protocol in Molecular Biology*, John Wiley & Son, 1989. The wells of a microtiter plate typically are coated with the peptide-specific (capture) antibodies, followed by incubation of the serum containing viral antigen. Unbound antigen is washed out and a different antigen conjugated to a detection vehicle, such as the enzyme, horseradish peroxidase, is added. The presence of the enzyme is then detected e.g. by reaction of the base substrate.

Antibodies raised against the HA-epitope chimeric proteins of the present invention can be used in these diagnostic methods and in diagnostic kits. Screening would be particularly effective using antibodies raised against the above described HA-HIV epitopes and HA-hepatitis B or C epitopes.

Similarly, one can test for the presence of antibodies by exposing a suspected sample such as blood or a fraction thereof to the chimetic antigens of the present invention.

The HA-epitope chimeric proteins of the present invention can also be used in immunotherapy. For example, pathogen-specific antibodies or neutralizing antibodies are raised against the HA-epitope proteins of the present invention to arrest infection and disease in cases where the subject has already been exposed to infection. This would include passive immunization, since immunoglobulins containing neutralizing antibodies against the infectious agent can be used to contain or control the infection. Examples of passive immunization include immunization against rabies in animals and humans, the treatment with monoclonal antibodies of septic shock syndrome caused by gram negative bacteria, and immunization against HIV.

The genomes coding for the chimeric proteins of the present invention can be inserted into expression vector systems. Suitable expression vectors include BPV (bovine papilloma virus) based expression vector, dihydrofolate reductase (dhfr)-related vector, adenovirus vector, or vaccinia viral vector. Special mention is made of baculovirus expression systems, such as *Autographa californica* nuclear polyhedrosis virus (AcMnPV) infected insect cells such as *Spodoptera frumperda* (Sf9).

During infection, the baculovirus makes large amounts of polyhedron protein, which promotes occlusions embedded with virus. The polyhedron gene has been shown to be nonessential for infection or replication of the virus. Deletion of this gene gives rise to occlusion-negative virus. The recombinant baculovirus is produced by homologous recombination between transfer vector and wild-type DNA. The transfer vector (e.g. pVL941) contains a viral DNA segment containing the polyhedron promoter (see Example 3). The gene to be expressed is inserted following the promoter sequence.

The inserted gene in the expression vector can be administered as a live viral vaccine such as an adenovirus or vaccinia virus vaccine. It can also be expressed in large quantities by transforming a suitable host such as *E. coli* and purifying.

All nucleotide sequences, peptides, and compositions incorporating them can be prepared by recombinant techniques or synthetically.

DESCRIPTIONS OF THE PREFERRED EMBODIMENTS

The following examples serve to illustrate the invention. The numbering of nucleotide and amino acid sequences of HA is according to Hiti, et al., *Virology*, 111:113–124, 1981. The HA gene is from the A/WSN/33 strain of human influenza virus. Routine recombinant DNA procedures for enzymatic reactions, plasmid DNA preparations, site-directed mutagenesis, bacterial and mammalian cell transformations, etc. were done according to suppliers's direction, or as described in Sambrook, et al., *Molecular Cloning A Laboratory Manual*, Cold Spring Harbor Laboratory Press, 1989. All parts and percentages are given by weight unless otherwise indicated.

Examples 1–7 illustrate the creation of an insertion site in the antigenic site A of HA where foreign epitopes are inserted to produce chimera proteins. Example 8 illustrates that, using similar strategy, it is possible to create insertion sites in the other known antigenic sites of HA. The foreign epitopes are then inserted in any of the newly created sites of HA. Example 8, in particular, illustrates the creation of a unique restriction site, BglII, at the aa 184/185 position of HA which is part of antigenic site B. Example 9 shows the use of multiple HA insertion sites.

EXAMPLE 1

CONSTRUCTION OF HA EXPRESSION VECTOR

Figure 2:
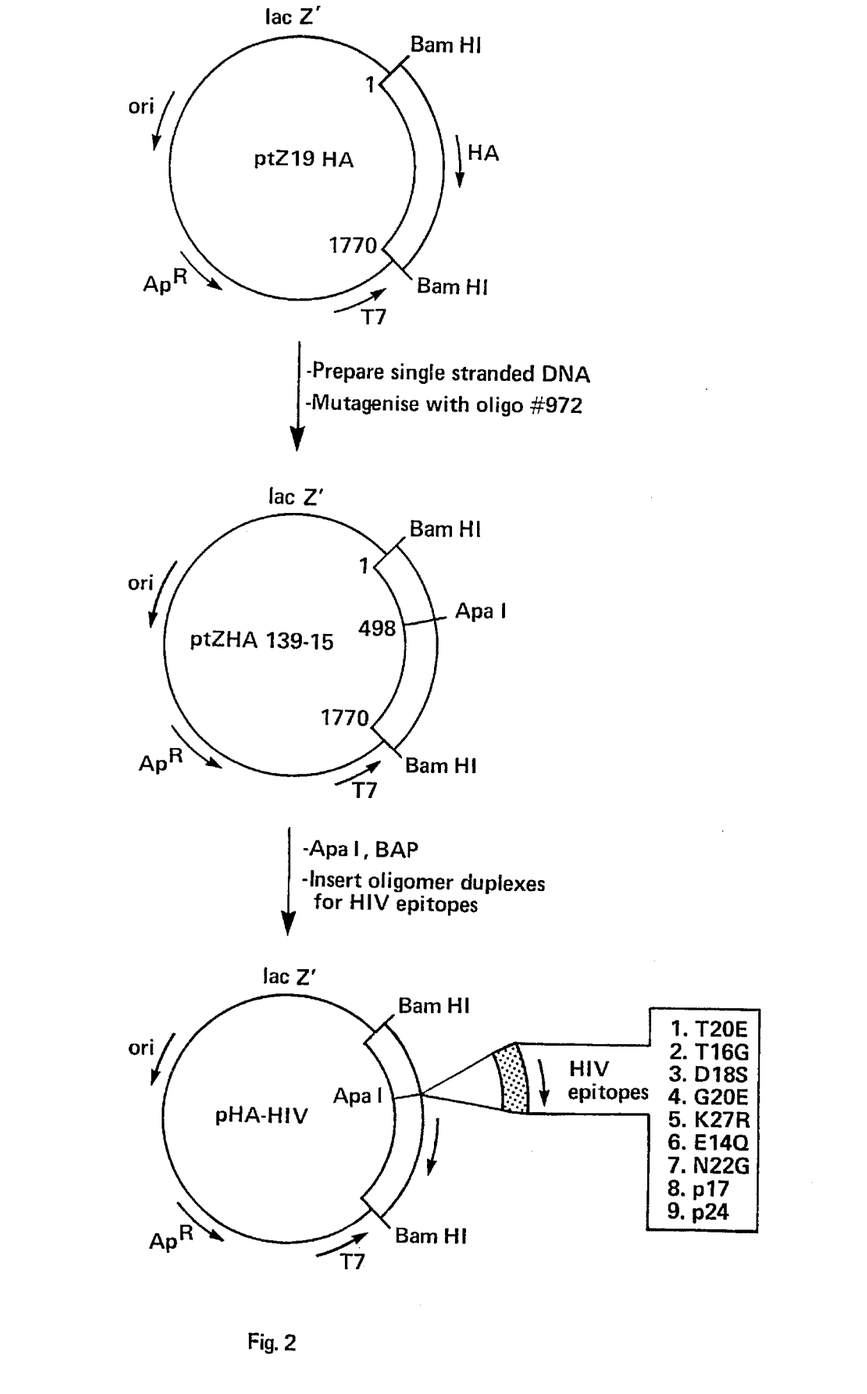
FIG. 2 is a schematic flow chart of the insertion of an exemplary HIV epitope into the HA gene with creation of an ApaI site at bp 498 (corresponding to aa 139) of the HA gene.

Reference is made to FIG. 2. The plasmid pHAX (also referred to as plasmid pSV-HA in Hartman, et at., *Proc. Natl. Acad. Sci. USA*, 79:233–237, 1982), carrying the complete coding sequence of HA gene, was digested with BamH1 to isolate 1.75 kb as a fragment. This DNA fragment encoding HA was then inserted into the BamH1 site of pTZ19R (Pharmacia, Inc.) to obtain a recombinant clone ptZ19HA.

Single stranded DNA, containing the HA sequence carded as a positive strand sequence, was isolated using ptZ19HA. Baldaft, et al., *Gene*, 35:27–32, 1985. This DNA was used to perform oligonucleotide-mediated site mutagenesis using the following oligonucleotide: 5'-TCT GTA AAA ACT GCT TTT TCG GGC CCT ATG GGA GCA TGA TAC -3'(#972). This oligonucleotide corresponds to bp 480–518 of the HA gene with the Apal site (GGGCCC) inserted in the middle. Mutagenesis with this oligonucleotide and transformation of E. coli JM109 cells were done according to published reports. Sambrook, et al., *Molecular Cloning A Laboratory Manual*, pp. 15–51, 1989. One clone, ptZHA139-15, was found to have the newly created ApaI site with gly 139, replaced with ala-arg while the rest of the sequence remained the same. This was confirmed by DNA sequencing of this region.

EXAMPLE 2

INSERTION OF PROTEIN EPITOPES

Reference is again made to FIG. 2. Complementary oligomers coding for different peptides were synthesized by the phosphotriester method. Crea, et al., *Proc. Natl. Acad. Sci. USA*, 70:5765, 1978. Equimolar concentrations of the complementary oligomers were mixed to get a duplex oligomer with flanking ApaI sequences. Before ligation, the oligomers were phosphorylated at the 5'-end with ATP and T4 DNA kinase, according to the supplier's instructions (Pharmacia, Inc.). About 10 µg of ptZHA139-15 was digested with ApaI and was dephosphorylated with bacterial alkaline phosphatase. Sambrook, et al., *Molecular Cloning, A Laboratory Manual*, 1989. About 100 ng of ApaI cut plasmid and 1 µg of oligonucleotides were individually ligated and used to transform *E.coli*. Bacterial colonies were screened using in situ hybridization with radiolabeled oligomers. Potential recombinant clones with inserts were then sequenced in order to determine correct orientation of the inserts as well as correct reading frames. Each of the nine HIV epitopes of Table 1 and FIG. 2 were used.

EXAMPLE 3

CONSTRUCTION OF RECOMBINANT BACULOVIRUS

Using standard recombinant DNA techniques (Sambrook, et al., *Molecular Cloning, A Laboratory Manual*, 1989), 1.75 kb HA or HA/HIV epitope chimera genes flanked by BamHI sequences were individually inserted into the AcMNPV-derived transfer vector pVL941 (obtained from Dr. Max D. Summers, and described in *A Manual of Methods for Baculovirus Vectors and Insect Cell Culture Procedures*, Texas A&M University, College Station, Tex., 1988). Expression of the heterologous protein gene is under the transcriptional control of the polyhedron promoter. A recombinant baculovirus containing the desired gene was generated by cotransfection of wild-type viral AcMNPV DNA (1 µg) and recombinant transfer plasmid DNA (2 µg) into Sf9 cells using a calcium phosphate precipitation method. Smith, G. E. et al., *Molec. Cell Biol.*, 3:2156–2165, 1983. Six days later, culture medium containing wild-type and recombinant baculovirus was harvested, and recombinant viruses were identified by limiting dilution method by hybridization to $^{32}$P-labeled HA gene of Sf9 cells infected with serially diluted virus in a 96-well plate. Germann, et al., *J. Biol. Chem.*, 264:7814–7824, 1989. Three to five rounds of hybridization screening were performed to obtain a pure occlusion negative (polyhedron-negative) virus, such as AcHA-N22G encoding the HA-N22G protein. This virus was propagated in Sf9 cells.

The Sf9 cells were seeded at a density of about $7 \times 10^7$ cells per T-150 (150 cm$^2$) flask. Alternately, Sf9 cells were grown as a suspension culture in a spinner flask to a density of 2 to $3 \times 10^6$ cells/ml. The cells were infected with recombinant virus at a multiplicity of infection (MOI) of 5–10. Three to four days later, when the expression of HA chimeras was at its maximum, the cells were harvested. After washing with PBS, the cells were extracted with 1% detergent mixture containing equal amounts of triton ×100 and deoxycholate to isolate membrane-bound HA or HA chimeras. Since HA is a glycoprotein, it was partially purified by passing the extract through an affinity column of lectin Sepharose 4B (lectin from lens culinaris, Sigma Chem. Co.—St. Louis, Mo). The partially purified HA or chimeras were used to immunize animals (guinea-pigs) to evaluate their efficacy as immunogens.

EXAMPLE 4

BIOLOGICAL PROPERTIES OF HA AND HA/HIV CHIMERA PROTEINS

High titer ($10^9$ pfu/ml) recombinant viruses were used to infect freshly plated Sf9 cells, which three days later were harvested and processed to isolate recombinant protein according to the method of Example 3. Recombinant proteins constituted about 10 to 20% of the total cellular protein as estimated from coomassie blue staining of gel. About 2 to 10% of recombinant protein was extractable by detergent and probably represented native form. The remainder was insoluble protein stored inside the cell. HA and HA-HIV chimera proteins were synthesized as triplet bands. The lower band (approximately 55 kD) represented unglycosylated form, since treatment of infected cells with tunicamycin, an inhibitor of glycosylation, produced only this protein band. The upper two bands (68 kD and 66 kD) probably represented different degrees of glycosylation processing. When recombinant HA baculovirus infected cells were extracted with detergent, only the 66 kD protein band was extractable, suggesting that this protein species is membrane associated and probably represents the native form of HA.

Immunofluorescence with rabbit anti-flu (A/WSN/33) serum and fluorescein-conjugated second antibody, goat anti-rabbit IgG, was performed. Posse, *Virus Res.*, 5:43–59, 1986. The cells infected with recombinant viruses showed strong membrane fluorescence. Mock-infected and wild-type infected cells failed to show any fluorescence.

Biological activities of the recombinant baculovirus infected Sf9 cells were assayed by hemadsorption and hemagglutination using 1% chicken RBCs. Posse, *Virus Res.*, 5:43–59, 1986. While the cells infected with recombinant HA baculovirus showed significant hemadsorption, others infected with wild-type or recombinant baculoviruses encoding HA-HIV chimeras (N22G, D18S, and T16G) did not show any activity in this assay. Similar results were obtained when hemagglutination was performed using cell detergent extracts. These results showed that the insertion of HIV epitope in HA affected the receptor binding site which mediates the biological activity of HA. The receptor binding site on HA is present near antigenic site A where the epitopes were selectively inserted (FIG. 1).

EXAMPLE 5

IMMUNE RESPONSE OF GUINEA PIGS INJECTED WITH HA-HIV CHIMERA PROTEINS

Sf9 cells in 20 to 30 T150 flasks were infected with recombinant baculovirus encoding HA-N22G and HA-D18S prepared according to the method of Example 3 at an MOI of 10. The cells were harvested at 72 hours post-infection, washed three times with PBS, and processed for purification. Partially purified HA or HA chimera proteins were used to immunize guinea pigs. Booster injections were given at four week intervals. Serum was collected two weeks after each injection.

The efficacy of the serum was determined by hemagglutination inhibition (HI) assay, which determines the ability of antiserum to inhibit hemagglutination reaction shown by 4 units of recombinant HA and 1% chicken RBC. All sera were first diluted 1:10 and treated with Kaolin (100 mg/ml per milliliter) to remove natural inhibitors. Kaolin treatment did not affect the antibody titer.

Results are illustrated in Table 2.

After the second injection, all of the sera against recombinant HA or HA-HIV chimera protein had HI titers ranging from 160 for N22G to 5120 for D18S. The control sera with no antigen had a titer of 20.

After the third injection, there was a further boost in HI titer in all animals. Animals immunized with crude plasma membrane prepared from cells infected with AcHA-N22G recombinant baculovirus also produced an HI titer of 60 to 80. An HI titer of 40 or more is considered as protective against influenza infection in human vaccination.

When the above experiment was repeated with HA of a heterologous flu strain (A+ Taiwan), no neutralization was observed. This shows that the baculovirus or expressed HA antigens were able to induce strain specific neutralizing antibodies. Additionally, the anti-sera against HA-D18S and HAN22G were shown to have antibodies reactive to HIV gp160, as shown in Western blot. Results of HA-N22G immunization are illustrated in Table 3.

Epitope N22G corresponds to the principal neutralizing domain of gp160 of HIV and is thus the main target for developing a vaccine. Javaherian, et al., *Proc. Natl. Acad. Sci. USA*, 86:6762–6772, 1989. Animal experiments were repeated using recombinant HA or HA-N22G. The animals were immunized initially with a partially purified preparation containing 1–2 μg of HA or chimera protein, and then boosted three times. Production of antibodies against the inserted peptide, N22G, was determined by (I) anti-peptide (N22G) ELISA, (II) Western blot with envelope gp160, and (III) in vitro neutralization assay (shown in Table 3). After second (2°) and third (3°) boosters, the animals showed productions of specific high titer antibodies in all three assays. As expected, animals immunized with HA did not show any activity in these assays. The production of neutralizing antibody against HIV infection in animals immunized with HA-N22G is of particular interest.

TABLE 2

Hemagglutination Inhibition (HI) Titers of Guinea-pig Serum Collected Two Weeks After Second (2°) and Third (3°) Injections

| Antigen | Guinea Pig# | Kaolin | HAI Titer 2° | HAI Titer 3° |
|---|---|---|---|---|
| HA | A | + | 1280 | 10240 |
|  | B | + | 1280 | 2560 |
| N22G | C | + | 160 | —[a] |
|  | D | + | 160 | — |
| D18S | E | + | 5120 | 10240 |
|  | F | + | 640 | 3790 |
| None[b] | 9 | + | 20 | 40 |
|  | 10 | + | 20 | 60 |
| N22G CrumbMemb | 11 | + | 80 | N.D.[c] |
| C. Pellet | 12 | + | 60 | N.D. |
| Flu WSN | Rabbit 313 | + | 5120 |  |
|  |  | − | 5120 |  |

[a]Both animals died during bleeding.
[b]The HI titer of normal serum without Kaolin treatment is 320.
[c]N.D. = not determined.

TABLE 3

Serological Analysis of Guinea Pigs Immunized
With HA and HA-N22G (HIVMN V3 Loop a.a. 307–330)
(Two animals per group were used)

| Assays | HA 1° | HA 2° | HA 3° | HA-N22G 1° | HA-N22G 2° | HA-N22G 3° |
|---|---|---|---|---|---|---|
| HA neutralization | 1280 | 2560 | 2560 | 160 | 640 | 2560 |
| titer (HI) | 1280 | 2560 | 5120 | 160 | 1280 | 1280 |
| HS ELISA titer | $10^6$ | $3 \times 10^5$ | $3 \times 10^5$ | $3 \times 10^5$ | $3 \times 10^5$ | $1 \times 10^5$ |
|  | $10^6$ | $3 \times 10^5$ | $1 \times 10^6$ | $3 \times 10^5$ | $1 \times 10^5$ | $1 \times 10^4$ |
| Anti-peptide (N22G) | − | − | − | 300 | 30,000 | 30,000 |
|  | − | − | − | 300 | 10,000 | 10,000 |
| anti-env (blot) | − | − | − | N.D. | 20,000 | >20,000 |
|  | − | − | − | N.D. | >1,000 | 20,000 |
| Neutralizing antibody | − | − | − | <10 | 40 | >810 |
| titer (Done at NIH) | − | − | − | <10 | 20 | 475 |

− = Negative
N.D. = Not done

EXAMPLE 6

IMMUNE RESPONSE OF CYNOMOLGUS MONKEYS INJECTED WITH HA-HIV CHIMERA PROTEINS

Twelve cynomolgus monkeys were immunized with HA-K17K ($HIV_{MN}$). They received 4 doses at one month intervals and were bled 2 weeks following each immunization. All twelve animals produced antibodies that recognized the peptide (ELISA) and that could neutralize the $HIV_{MN}$ isolate in vitro (Table 4). The best results were obtained in those animals which received 100 μg in Syntex adjuvant, which is consistent with rodent data. One animal from the 100 μg Syntex group and one from the 100 μg liposome group were compared for the anti-HA titers (Table 5). Again, the animal treated with the Syntex adjuvant produced higher antibody titers than the monkey treated with the liposome adjuvant.

TABLE 4

Cynomolgus Monkey HA-HIV (K17K) Immunization

| Monkey | Adjuvant | Dose | ELISA | HIV-1 Neutralizing Titer |
|---|---|---|---|---|
| E121A | Syntex | 100 μg | 100–1000 | 50 |
| 128C | " | 100 μg | 1000–10,000 | 150 |
| D759A | " | 100 μg | 1000–10,000 | 150 |
| C188B | " | 10 μg | 100–1000 | 55 |
| 1786 | " | 10 μg | ≦100 | 25 |
| 30C | " | 10 μg | 100–1000 | 45 |
| D415A | Liposomes | 100 μg | ≦100 | 20 |
| 1851 | " | 100 μg | 100–1000 | 45 |
| 19E | " | 100 μg | ≦100 | 15 |
| 217D | " | 10 μg | ≦100 | 45 |
| 1518 | " | 10 μg | ≦100 | 15 |
| 81D | " | 10 μg | ≦100 | 10 |

TABLE 5

Antibody Levels in Cynomolgus Monkeys Immunized with HA-HIV (K17K)

| Animal | Dose (Amount No.) | Adjuvant | Anti-HA Titer[1] (HA Region) |
|---|---|---|---|
| 1 | pre-immune | | <1000 |
| 1 | 100 μg/first | Syntex | 10,000–100,000 |
| 1 | 100 μg/second | Syntex | >1,000,000 |
| 1 | 100 μg/third | Syntex | >1,000,000 |
| 1 | 100 μg/fourth | Syntex | >1,000,000 |
| 2 | 100 μg/first | liposomes | — |
| 2 | 100 μg/second | liposomes | — |
| 2 | 100 μg/third | liposomes | ~100,000 |
| 2 | 100 μg/fourth | liposomes | ~100,000 |

[1]Done by immunoblot with hemagglutinin extracted from influenza WSN.

EXAMPLE 7

PREPARATION OF HA-IgE (HA-K11OF) EPITOPE

The cloning of a recombinant HA gene into the baculovirus transfer vector, pBL1 (Vialard, et al., *J. Virology*, 69:37-50, 1990), was facilitated by modifying the flanking restriction sites. About 2 μg of ptZHA-139-15 was digested with BamH1 to isolate 1.75 kilobase DNA fragments. This DNA fragment, after fill-in with a DNA polymerase Klenow fragment and deoxynucleotide triphosphates (dNTP), was inserted into Hind III/filled in pGEM-9Zf(−) plasmid (Promega Biotec Madison, Wis.) to get pHA.Nhel. From this plasmid, HA or chimera HA genes were excised as a 1.75 kilobase DNA fragment after digestion with Spel and Xbal.

About 1 μg of pHA.Nhel plasmid DNA was digested with Apal and then dephosphorylated with bacterial alkaline phosphatase. Two complimentary oligonucleotides coding for the K1OF peptide were synthesized:

```
      K   T   K   G   S   G   F   F   V   F
5'    AAA ACC AAG GGA TCA GGA TTC TTT GTA TTC GGG GCC 3'
CCGG  TTT TGG TTC CCT AGT CCT AAG AAA CAT AAG CC
           Sty 1                                  Apa 1
```

Equal molar amounts of the two oligomers were mixed and phosphorylated using T4 polynucleotide kinase and ATP. About 0.1 μg of dephosphorylated vector and 1 μg of duplex oligomers were ligated and then used to transform *E. coli* MM294 cells.

Miniprep from twelve clones were prepared and digested with StyI to screen for the presence of the inserted oligomers. One clone, pHA.Nhe-hIgE-11 was found to have the inserted nucleotide sequence in the correct coding sequence. Nucleotide sequencing confirmed the correct sequence at the desired site. About 10 μg of this plasmid were digested with Spel and Xbal together to isolate 1.8 kilobase DNA fragment.

About 10 micrograms of baculovirus transfer vector, pBlueBac (pBL1 Invitrogen Corp.—San Diego, Calif.) were digested with Nhel and dephosphorylated with BAP. About equal molar amounts of the Nhel cut vector and the 1.8 kb DNA were ligated, and the ligation mixture was used to transform *E. coli* MM294 cells. Twelve clones were selected to prepare mini-plasmid preparations. One clone, pBL-HA-KlOF-5-2, was identified to have the HA.K1OF gene in the correct orientation.

To obtain the recombinant baculovirus, about 1 μg of wild-type virus, AcMNPV, DNA, and 2 μg of recombinant transfer vector, pBL-HA-KlOF-5-2, were used to transfect Sf9 insect cells using a calcium phosphate precipitation method. Summers, et al., *A Manual of Methods for Baculovirus Vectors and Insect Cell Culture Procedures*, Texas A&M University, College Station, Tex., 1988. The recombinant baculovirus was generated by homologous recombination between the transfer vector and the wild-type viral DNA. Six days after transfection, the medium containing a mixture of wild-type and recombinant virus was harvested. The medium, after serial dilution ($10^{-3}$–$10^{-6}$) was used to infect freshly plated SF9cells in 100 millimeter petri dishes which were then overlaid with agarose containing betagalactosidase substrate, X-gal. The recombinant virus, indicated by the presence of blue plaque, was further purified by several rounds of plaque purification. Vialard, et al., *J. Virology*, 69:37–50, 1990. This recombinant baculovirus was named AcHA.KlOF. Expression of the chimera protein HAK1 OF was determined by Western blot analysis of proteins of infected Sf9 cells using antibodies raised against the peptide. After culturing for a large scal production and purification, the chimera was used as a vaccine,

EXAMPLE 8

PREPARATION OF HA-IqE (HA-H22V) EPITOPE

A nucleotide sequence coding for peptide H22V was inserted into the HA gene which was then expressed in baculovirus expression systems according to the procedure of Example 6. Two complementary oligonucleotides were synthesized unique restriction sites mentioned here are meant to include sites which are not present in either HA or plasmid ptZ19R

| Apa 1 | H | S | T | T | Q | P | R | K | T | K | | |
|---|---|---|---|---|---|---|---|---|---|---|---|---|
| | CAC | AGT | ACT | ACA | CAG | CCC | CGC | AAA | ACC | AAG | | |
| CCGG | GTG | TCA | TGA | TGT | GTC | GGG | GCG | TTT | TGG | TTC | | |
| G | S | G | F | F | V | F | S | R | L | E | V | |
| GGA | TCA | GGA | TTC | TTT | GTA | TTC | TCA | CGC | CTA | GAG | GTG | GCC |
| CCT | AGT | CCT | AAG | AAA | CAT | AAG | AGT | GCG | GAT | CTC | CA | |

The duplex oligomer was inserted at the ApaI site of pHA.NheI to get recombinant pHA-Nhe-H22V. A 1.8 kilobase SpeI/XpaI DNA fragment obtained from the aforementioned plasmid was inserted into the NheI site of pBL1 to obtain a recombinant transfer plasma, pBL-HA-H22V-1. By a homologous recombination of this plasmid and AcMNPV DNA, a recombinant baculovirus, AcHA-H22V, was obtained. This recombinant baculovirus, after infection of Sf9 cells, expressed HA- H22V chimera protein which, after purification, can be used as a vaccine.

EXAMPLE 9

CONSTRUCTION OF HA EXPRESSION VECTOR WITH INSERTION SITE CREATED AT SITES B, C, D, AND E

Using recombinant plasmid ptz19HA, carrying HA gene, single stranded DNA was prepared. baldari, et al., *Gene,* 35:27–32, 1985. This DNA was used to perform site directed mutagenesis with the following oligomer: 5' ACT CTG TTG CTC AGA TCT GCT GGA CGG GTG ATG AAC 3'. This oligonucleotide corresponds to bp 615–650 (aa 178–189) of HA gene with the BglII restriction site (AGATCT) inserted in the middle of the oligonucleotide. Mutagenesis with this oligo and transformation of *E. coli* JM109 were done according to the published report Sambrook, et al., *Molecular Cloning, A Laboratory Manual,* pp. 15–51, 1989. One clone, pt2HA184-1, was found to have the newly created BglII site. This was confirmed by DNA sequencing of this region. Mutagenesis resulted in the substitutions of ser 184 and asp 185 with the arg and ser residues, respectively, while the rest of the sequence remained unchanged.

EXAMPLE 10

CONSTRUCTION OF HA EXPRESSION VECTOR WITH MULTIPLE INSERTION SITES

Two insertion sites, one each at antigenic sites A and B of HA, were created where two epitopes of the same or different sequences can be inserted. Recombinant plasmid, ptZHA139-1S, described in Example 1, contains the HA gene where a unique restriction sire, ApaI, is created at the sequence corresponding to antigenic site A. Single stranded DNA prepared from this plasmid was used to mutagenize with the oligomer sequence of Example 8 which was designed to create a unique BglII recognition sequence at site B. One clone, pHA139/184, was found to have both the newly created sites ApaI and BglII, which were subsequently confirmed by DNA sequencing of the relevant regions. The same or a different foreign epitope is then inserted in any one of the known antigenic sites of HA.

The procedure of Example 9 can be extended to include creating additional unique restriction sites in regions corresponding to antigenic sites C, D, and/or E of HA as well. The sequences. Besides ApaI and BglII, other examples of unique restriction sites are AflIII, AvrII, BclII, NheI, XhoI, etc.

EXAMPLE 11

PASSIVE IMMUNIZATION WITH ANTI-N22G ANTIBODIES TO PREVENT HIV INFECTION

Passive immunization is useful in cases where there is accidental exposure of a subject to infected blood or any of the blood-derived components. The application is also useful for maternal-fetal transmission of HIV. Administration of HIV-1 V3 loop (N22G) specific antibodies would prevent establishment of infection. Berzofsky, J. A., et al., "Approaches and Issues in the Development of Vaccines Against HIV," *J. Acquired Immune Deficiency Syndromes,* 4:451–459, 1991.

In order to obtain large amounts of N22G peptide-specific antibodies, large animals (e.g., horses) are immunized with multiple injections until high titer neutralizing antibodies against HIV-1 are obtained as described in Example 5 and Table 3. The animals are bled to obtain sera which is then passed through an affinity column of Protein A Agarose to enrich the IgG fraction according to the supplier's instruction (GIBCO BRL, Life Technology, Inc., Gaithersburg, Md.). IgG fraction contains HIV-1-specific antibodies. A suitable amount of IgG formulated in an appropriate carrier is injected in persons suspected of HIV-1 exposure. The dosage and timing of injection is determined by clinical trials in humans.

The above mentioned patents, publications, and test methods are incorporated herein by reference.

Many variations of the present invention will suggest themselves to those skilled in the art in light of the above detailed description and are within the scope of the invention and appended claims.

What is claimed is:

1. A peptide comprising an amino acid sequence substantially the same as the HA surface protein of an influenza A virus, said surface protein having five immunodominant antigenic sites, wherein an amino acid sequence substantially the same as that of a foreign epitope is inserted into the amino acid sequence for at least one antigenic site.

2. A peptide as in claim 1, wherein the antigenic site is selected from the group consisting of the A region, B region, C region, D region, and E region of HA protein.

3. A peptide as in claim 2, wherein the antigenic site is the A region of said HA protein.

4. A peptide as in claim 1, wherein the antigenic site in which said foreign epitope is inserted corresponds to amino acids 183–192 of HA protein.

5. A peptide as in claim 1, wherein the foreign epitope is selected from the group consisting of viral epitopes, IgE effector site epitopes, bacterial protein epitopes, and SP10 epitopes.

6. A peptide as in claim 5, wherein the viral epitope is selected from the group consisting of T20E, T16G, D18S, G20E, K27R, E14Q and N22G, P17, P24, gp160, and gp120.

7. A pharmaceutical composition comprising a peptide as defined in claim 5 and an adjuvant or pharmaceutically acceptable carrier.

8. A pharmaceutical composition comprising a polypeptide corresponding to the amino acid sequence of the HA surface protein of an influenza A virus containing a foreign epitope in an immunodominant antigenic site, said foreign epitope being selected from the group consisting of viral epitopes, IgE effector site epitopes, bacterial protein epitopes, and SP10 epitopes and an adjuvant or pharmaceutically acceptable carrier.

9. A pharmaceutical composition comprising a mixture of polypeptides, each corresponding to the amino acid sequence of the HA surface protein of an influenza A virus containing a foreign viral epitope in an immunodominant antigenic site, said foreign epitopes being selectively antigenic and in correspondence to different HIV strains, to thereby induce the production of a family of antibodies in response to said HIV strains.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 36 base pairs
        ( B ) TYPE: nucleic acid
        ( C ) STRANDEDNESS: double stranded
        ( D ) TOPOLOGY: unknown     ( i i ) FEATURE:
        ( A ) OTHER INFORMATION: Anti-sense strand begins four
            bases before the sense strand,
            adding the sequence CCGG and
            ends four bases before the
            sense strand.

( i i i ) SEQUENCE DESCRIPTION: SEQ ID NO:1:

```
AAA  ACC  AAG  GGA  TCA  GGA  TTC  TTT  GTA  TTC  GGG  GCC         36
Ala  Thr  Ala  Gly  Ser  Gly  Phe  Phe  Val  Phe
1              5                        10
```

( 2 ) INFORMATION FOR SEQ ID NO:2:

( i ) SEQUENCE CHARACTERISTICS:
        ( A ) LENGTH: 69 base pairs
        ( B ) TYPE: nucleic acid
        ( C ) STRANDEDNESS: double stranded
        ( D ) TOPOLOGY: unknown     ( i i ) FEATURE:
        ( A ) OTHER INFORMATION: Anti-sense strand begins four
            bases before the sense strand,
            adding the sequence CCGG and
            ends four bases before the
            sense strand.

( i i i ) SEQUENCE DESCRIPTION: SEQ ID NO:2:

```
CAC  AGT  ACT  ACA  CAG  CCC  GGC  AAA  ACC  AAG              30
His  Ser  Thr  Thr  Gln  Pro  Arg  Lys  Thr  Lys
1              5                        10

GGA  TCA  GGA  TTC  TTT  GTA  TTC  TCA  CGC                   57
Gly  Ser  Gly  Phe  Phe  Val  Phe  Ser  Arg
15

CTA  GAG  GTG  GCC                                            69
Leu  Glu  Val
20
```

( 2 ) INFORMATION FOR SEQ ID NO:3:

( i ) SEQUENCE CHARACTERISTICS:
        ( A ) LENGTH: 42 bases
        ( B ) TYPE: nucleic acid
        ( C ) STRANDEDNESS: single stranded
        ( D ) TOPOLOGY: linear     ( i i ) SEQUENCE DESCRIPTION: SEQ ID NO:3:

```
TCTGTAAAAA  CTGCTTTTTC  GGGCCCTATG              30

GGAGCATGAT  AC                                  42
```

( 2 ) INFORMATION FOR SEQ ID NO:4:

( i ) SEQUENCE CHARACTERISTICS:
        ( A ) LENGTH: 36 bases
        ( B ) TYPE: nucleic acid
        ( C ) STRANDEDNESS: single stranded (D) TOPOLOGY: linear (ii) SEQUENCE DESCRIPTION: SEQ ID NO:4:

ACTCTGTTGC TCAGATCTGC TGGACGGGTG ATGAAC    36